United States Patent [19]

Johnson et al.

[11] Patent Number: 5,969,805
[45] Date of Patent: Oct. 19, 1999

[54] METHOD AND APPARATUS EMPLOYING EXTERNAL LIGHT SOURCE FOR ENDPOINT DETECTION

[75] Inventors: David R. Johnson, Meridian; Joe Lee Phillips, Nampa; Todd C. Nielsen, Meridian; Robert J. Hatfield, Boise, all of Id.

[73] Assignee: Micron Technology, Inc., Boise, Id.

[21] Appl. No.: 08/963,508

[22] Filed: Nov. 4, 1997

[51] Int. Cl.$^6$ ............................. G01B 11/00; G01B 11/06
[52] U.S. Cl. .................... 356/72; 356/381; 250/559.27; 216/60
[58] Field of Search .................... 356/72, 73, 381, 356/382; 250/559.27; 216/58, 60

[56] References Cited

U.S. PATENT DOCUMENTS

| | | |
|---|---|---|
| 4,377,436 | 3/1983 | Donnelly et al. . |
| 4,462,863 | 7/1984 | Nishimatsu et al. . |
| 4,482,424 | 11/1984 | Katzir et al. .............................. 216/80 |
| 4,586,822 | 5/1986 | Tanimoto . |
| 4,609,428 | 9/1986 | Fujimura . |
| 4,846,920 | 7/1989 | Keller et al. . |
| 5,162,867 | 11/1992 | Kohno . |
| 5,176,790 | 1/1993 | Arleo et al. . |
| 5,257,047 | 10/1993 | Haneda et al. . |
| 5,264,328 | 11/1993 | DellaGuardia et al. . |
| 5,312,717 | 5/1994 | Sachdev et al. . |
| 5,350,236 | 9/1994 | Thakur et al. . |
| 5,362,356 | 11/1994 | Schoenborn . |
| 5,397,431 | 3/1995 | Kadomura . |
| 5,434,026 | 7/1995 | Takatsu et al. . |
| 5,444,265 | 8/1995 | Hamilton . |
| 5,447,598 | 9/1995 | Mihara et al. . |
| 5,483,568 | 1/1996 | Yano et al. . |
| 5,489,362 | 2/1996 | Steinhardt et al. . |
| 5,552,016 | 9/1996 | Ghanayem . |
| 5,567,268 | 10/1996 | Kadomura . |
| 5,654,237 | 8/1997 | Suguro et al. . |
| 5,672,091 | 9/1997 | Takahashi et al. . |

FOREIGN PATENT DOCUMENTS 4-280650  10/1992  Japan ........................................ 356/72

*Primary Examiner*—F. L. Evans
*Attorney, Agent, or Firm*—Trask, Britt & Rossa

[57] ABSTRACT

A method and apparatus for endpoint detection for the stripping of a particular material, such as photo-resist material, from a substrate surface. A beam of light is projected onto the substrate surface and the fluoresced and/or reflected light intensity at a particular wavelength band is measured by a light detector. The light intensity is converted to a numerical value and transmitted electronically to a control mechanism which determines the proper disposition of the substrate. The control mechanism controls the cessation of the stripping process and may control a substrate-handling device which sequentially transfers substrates to and from a stripping chamber.

42 Claims, 2 Drawing Sheets

METHOD AND APPARATUS EMPLOYING EXTERNAL LIGHT SOURCE FOR ENDPOINT DETECTION

BACKGROUND OF THE INVENTION

1. Field of the Invention

This invention relates generally to the manufacture of semiconductor devices prepared by a method including photolithography. More particularly, this invention pertains to a method for inspecting semiconductor substrates to determine the completion of stripping ("endpoint") during a plasma stripping process to remove a photo-resist material from a semiconductor substrate surface after photolithography.

2. State of the Art

Semiconductor chips are produced in a multi-step process by which a plurality of identical electronic circuits is typically formed on a semiconductor substrate, such as a silicon wafer. The semiconductor substrate is then subdivided (diced) into individual chips which are further processed into packaged semiconductor devices or otherwise secured in higher-level packaging for ultimate use.

The electronic circuits are generally patterned into a semiconductor substrate by a series of steps including photolithography. To elaborate, a photo-resist material is coated onto the semiconductor substrate surface. As disclosed in commonly owned U.S. Pat. No. 5,350,236 issued Sep. 27, 1994, hereby incorporated herein by reference, the temperature of a semiconductor substrate during the application of a material can be monitored by measuring light reflected from a surface of the semiconductor substrate, such that the material and semiconductor substrate are not overheated.

After the photo-resist material has been coated on the semiconductor substrate surface, it is selectively exposed to a radiation source, such as by the passage of radiation (i.e., light, e-beam, or X-rays) through a mask having a desired aperture pattern defined therein. If a positive photo-resist material is used, the exposure to the radiation source converts the positive photo-resist material to a more soluble state which allows the exposed positive photo-resist to be removed with a solvent, thereby leaving a pattern substantially identical to the mask. If a negative photo-resist material is used, the exposure to the radiation source converts the negative photo-resist material to a less soluble state which allows the unexposed positive photo-resist to be removed with a solvent, thereby leaving a pattern substantially identical to the openings in the mask. Whether a positive or a negative photo-resist material is used, the photolithographic process results in a photo-resist pattern which will become the electronic circuit pattern on a semiconductor substrate.

Following the removal of the portions of the photo-resist material in the development process, the semiconductor substrate is subjected to further processing steps which may include doping, etching, and/or deposition of conductive materials in unprotected areas, i.e., areas devoid of photo-resist material. After one or more of these processing steps, the semiconductor substrate is subjected to a stripping step to remove the photo-resist material remaining on the semiconductor substrate.

The stripping of photo-resist material is commonly achieved using plasma etching. In plasma etching, a glow discharge is used to produce at least one reactive species, such as atoms, radicals, and/or ions, from relatively inert gas molecules. Basically, a plasma etching process comprises 1) is generated at least one reactive species in a plasma from a bulk gas, 2) the reactive species diffuses to a surface of a material being etched, 3) the reactive species is absorbed on the surface of the material being etched, 4) a chemical reaction occurs which results in the formation of at least one volatile by-product, 5) the by-product is desorbed from the surface of the material being etched, and 6) the desorbed by-product diffuses into the bulk gas. The materials used as photo-resist are generally organic polymers, such as phenol-formaldehyde, polyisoprene, poly-methyl methacrylate, poly-methyl isopropenyl ketone, poly-butene-1-sulfone, poly-trifluoroethyl chloroacrylate, and the like. Such photo-resist materials are generally etched in plasmas containing pure oxygen to produce species that attack the organic materials to form $CO$, $CO_2$, and $H_2O$ as volatile by-products.

After the removal of the photo-resist material, a subsequent processing step may include heating the semiconductor substrate in a diffusion furnace or applying a layer of material with a chemical vapor deposition system. Occasionally, a semiconductor substrate is inadvertently passed to a thermal furnace or vapor deposition system with incomplete removal of the photo-resist material. The resulting damage to the processing equipment may be severe. For example, furnace diffusion tubes are irreparably damaged by vaporized hydrocarbons and carbon from the photo-resist material and, thus, the furnace diffusion tubes must be replaced. The replacement equipment and/or the downtime to repair the processing equipment is usually very costly.

Furthermore, the photo-resist carrying semiconductor substrate and one or more subsequent semiconductor substrates entering the processing equipment prior to shutdown of the equipment are usually also contaminated and must be discarded. At a late stage of manufacture, a semiconductor substrate may have a value between about $10,000 and $20,000. Thus, even an occasional loss is significant.

Therefore, it is very important that completion ("endpoint") of the photo-resist stripping be accurately detected. A common endpoint detection method with plasma etching is disclosed in U.S. Pat. No. 4,377,436 issued Mar. 22, 1983 to Donnelly et al. wherein endpoint detection during plasma-assisted etching is signaled by cessation or onset of spatially confined luminescence resulting from an etch reaction product. The light source for the luminescence comes from the plasma generation. However, as the use of microwave plasma etching has developed, the generation of the plasma has been removed from the etching chamber. The removal of the plasma generation from the etching chamber prevents excess heat buildup in the etching chamber caused by the plasma generation and allows for different frequencies and wavelengths to be used to create free radials (i.e., the reactive species).

The reactive species is formed remotely in a microwave reaction chamber and transported to the etching chamber, such as shown in U.S. Pat. No. 5,489,362 issued Feb. 6, 1996 to Steinhardt et al. No plasma is present in the stripping chamber with such a microwave plasma system. Therefore, there is no light source present in the chamber that can be used for detection of the endpoint removal of the photo-resist material.

Therefore, it would be advantageous to develop an apparatus and method of luminescent endpoint detection for the stripping of materials in a microwave plasma etching system employing a plasma chamber separate from its etching chamber.

SUMMARY OF THE INVENTION

The present invention is an automated method and apparatus for determining the endpoint of the removal of a photo-resist material on the surface of a semiconductor substrate by the detection of fluorescence, reflection, or absorption of light by the photo-resist material. Hereinafter, the term "emanated light" is defined as the light resulting from a light striking the photo-resist material or other material including fluoresced light, reflected light, or absorbed light.

As mentioned above, photo-resist materials are generally organic polymers, such as phenol-formaldehyde, polyisoprene, poly-methyl methacrylate, poly-methyl iso-propenyl ketone, poly-butene-1-sulfone, poly-trifluoroethyl chloroacrylate, and the like. Organic substances can generally fluoresce (luminescence that is caused by the absorption of radiation at one wavelength followed by nearly immediate re-radiation at a different wavelength) or will absorb or reflect light. Fluorescence of the photo-resist material at a particular wavelength, or reflection/absorption by the photo-resist material of light at a given wavelength, may be detected and measured, provided the material differs from the underlying semiconductor substrate in fluorescence or reflection/absorption at a selected wavelength or wavelengths. For example, a positive photo-resist generally fluoresces red or red-orange and a negative photo-resist generally fluoresces yellow.

In a particular application of the invention, the presence of photo-resist material on a semiconductor substrate surface may be rapidly and automatically determined, recorded, and used to determine when the photo-resist material has been removed from the semiconductor substrate surface. In a preferred application of the present invention, a semiconductor substrate is introduced into a stripping chamber which receives at least one reactive species, usually generated from oxygen, from a microwave plasma generator. The stripping chamber includes a first optical port and a second optical port positioned in a wall of the stripping chamber. A beam of light from a lamp passes through the first port, strikes the photo-resist material on the semiconductor substrate and is reflected as an emanated beam at an angle through the second optical port. Preferably, the photo-resist material differs from the semiconductor substrate in fluorescence, absorption, and/or reflection properties at some wavelengths of incident light.

The intensity of the emanated light will decrease when the photo-resist is stripped away. When the intensity has decreased to a level indicating that the photo-resist has been completely stripped away, the stripping process can be terminated. This detection method also allows the system to generate an error signal if the level indicating that the photo-resist has been stripped is not reached within a certain amount of time. Such an error signal would indicate that a semiconductor substrate was stripping poorly (i.e., too slowly) or the stripping equipment was not functioning properly. This error signal allows for the culling of the offending semiconductor substrate for rework or allows for the stripping equipment to be shut down for repair, which prevents the spread of photo-resist material contamination throughout other process steps. Furthermore, the throughput of the stripping equipment can be increased because empirically established finite strip times used in conjunction with endpoint detection of the photo-resist removal prevents the need for exaggerated strip times to ensure complete stripping.

In this invention, the semiconductor substrate is irradiated with light, which light may be monochromatic, multichromatic, or white. In one variation, the intensity of generated fluorescence particular to the photo-resist material at a given wavelength is measured. In another variation, the intensity is measured at a wavelength which is largely or essentially fully absorbed by the photo-resist material. In a further variation, the intensity of reflected light is measured at a particular wavelength highly reflected by the photo-resist material but absorbed by the substrate.

The intensity of the emanated light is measured by a sensing apparatus and the result inputted to a logic circuit, e.g., a programmable computer. The result may be recorded and used for a decision making step or to activate a culling device.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE PREFERRED EMBODIMENTS

Figure 1:
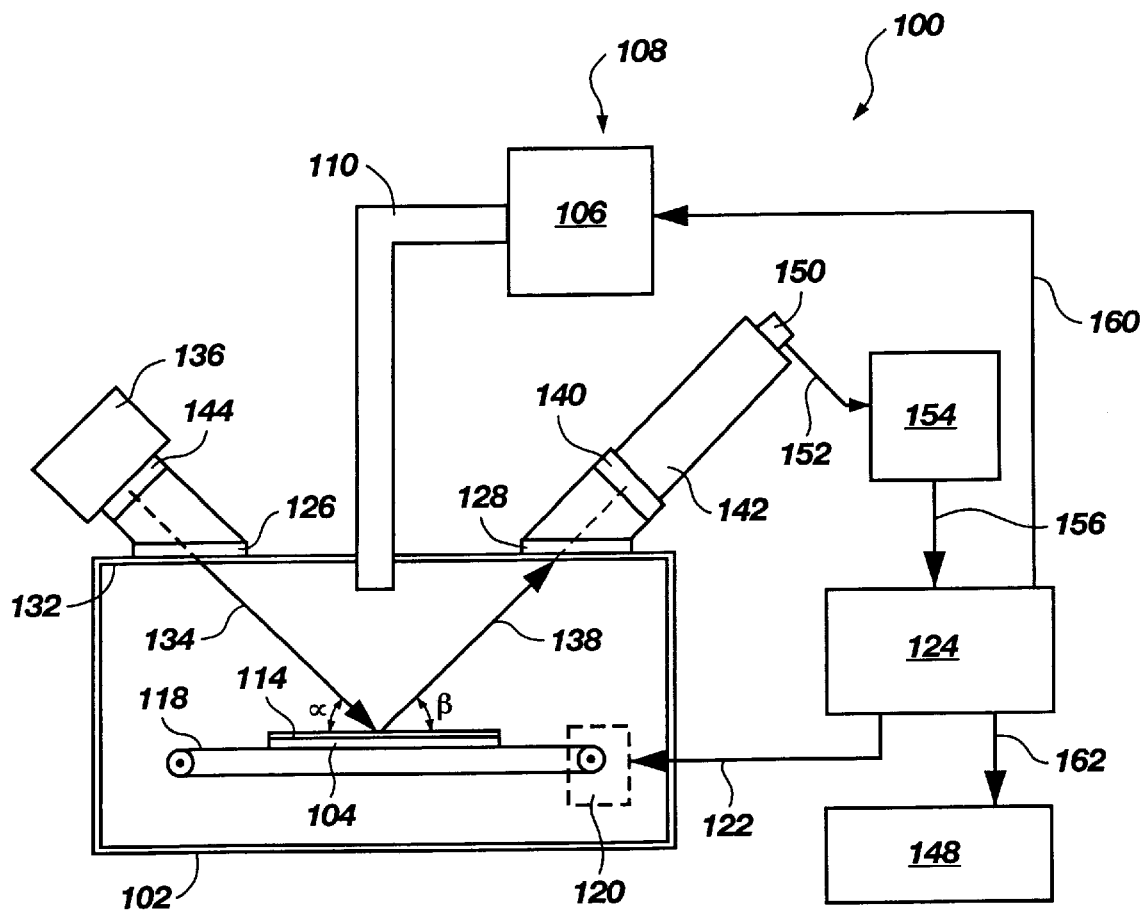
FIG. 1 is a diagrammatic view of a photo-resist material stripping apparatus of the present invention.

FIG. 1 illustrates a stripping apparatus 100 of the present invention. It should be understood that the apparatus 100 of FIG. 1 is not meant to be an actual view of any particular stripping device, but is merely an idealized representation which is employed to more clearly and fully depict the process of the invention than would otherwise be possible.

The stripping apparatus 100 comprises a stripping chamber 102 having one or more entryways or portals (not shown) for the introduction and removal of semiconductor substrates, such as semiconductor substrate 104, into and from the stripping chamber 102. The semiconductor substrate 104 may be a semiconductor material comprising a slice of crystalline silicon (silicon wafer) or may include various semiconductive material or material layers, including without limitation silicon wafers, silicon-on-insulative (SOI) structure, silicon-on-sapphire (SOS) structure, gallium arsenide, or germanium.

The stripping apparatus 100 also includes a microwave plasma generator 106 which generates reactive species in a plasma from an oxygen containing gas 108 fed to the plasma generator 106. The reactive species travel down waveguide 110 into the stripping chamber 102.

A photo-resist material detection apparatus is integrated with the stripping chamber 102 for in situ automated determination of the progress in stripping of a photo-resist material 114 from the semiconductor substrate 104. Preferably, the photo-resist material 114 differs from the semiconductor substrate 104 in flourescing, absorption, and/ or reflection properties at some wavelengths of incident light. The semiconductor substrate 104 is shown on a movable stage 118 within the stripping chamber 102 to provide the desired positioning of the semiconductor substrate 104 with respect to a primary high energy beam 134. The movable stage 118 may be movable by one or more stepper motors 120 (shown in shadow lines) or other motive means controlled by electronic signals 122 from a control mechanism 124, such as a programmed general purpose computer, i.e., a personal computer driving appropriate switches.

Figure 2:
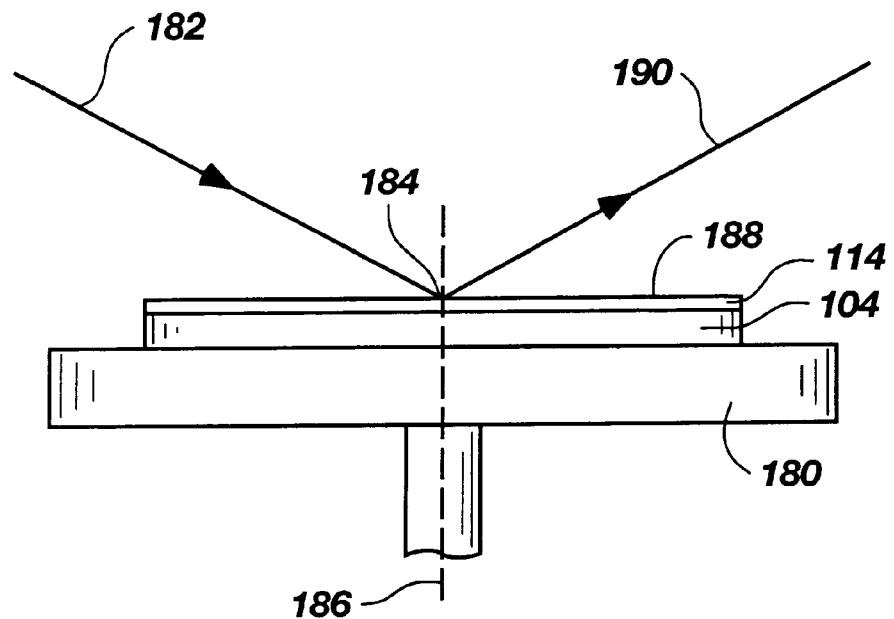
FIG. 2 is a side view of an alternate photo-resist material stripping apparatus of the present invention.

The photo-resist material detection apparatus includes two optical ports, a first optical port 126 and a second optical port 128, which are positioned in an upper wall 132 of the stripping chamber 102. The primary high energy beam 134 of light from a high energy lamp 136 passes through the first port 126, strikes the photo-resist material 114 of the semiconductor substrate 104 at an angle of incidence α and is reflected as an emanated beam 138 at an angle of departure β (substantially equal to angle of incidence α) through the second optical port 128. Although the beam 134 may irradiate the entire surface of the semiconductor substrate 104 simultaneously, the beam 134 is preferably a sheet beam having a width (perpendicular to the plane of the drawing sheet) approximately the width of the semiconductor substrate 104. The semiconductor substrate 104 can be passed under the sheet beam using movable stage 118, enabling the inspection of the entire surface of the semiconductor substrate 104. Furthermore, as illustrated in FIG. 2, the semiconductor substrate 104 can be positioned on a rotating platform 180, wherein a sheet beam 182 is directed to a center point 184 of the photo-resist material 114 on the semiconductor substrate 104 and extends across the width (perpendicular to the plane of the drawing sheet) of the semiconductor substrate 104 resulting in emanated beam 190. The rotatable platform 180 is rotated about axis 186 such that the entire surface 188 of the photo-resist material 114 is contacted by the sheet beam 182. This allows for different perspectives of the photo-resist material surface 188 which will detect photo-resist material 114 that may be in a "shadow" due to the topography of the semiconductor substrate 104, if only one particular perspective is taken.

Fluoresced and/or reflected light produced by existing photo-resist material 114 in response to the beam 134 is also present in the emanated beam 138. The emanated beam 138 may be passed through an optical band pass filter or suppression filter 140 to absorb non-fluoresced light or undesired reflected light and produce a filtered light beam substantially free of such undesired wavelengths. For example, the emanated beam 138 may be passed through the optical band pass filter 140 to produce a light beam having a narrow wavelength band of, for example, 700 nm±80 nm. Such a wavelength is a characteristic fluorescing emission of commonly used positive photo-resist materials, as listed above.

The emanated beam 138 is transmitted into a photomultiplier tube 142 for the ultimate generation of an electronic signal 156 indicative of the light intensity at the filtered light wavelength. The electronic signal 156 may be generated by a light intensity sensor 150, such as a silicon diode sensor, which generates an analog intensity signal 152. The intensity signal 152 is sent to a power meter 154 including an analog-to-digital converter, which converts the intensity signal 152 into an electronic binary numerical value comprising the electronic signal 156. The electronic signal 156 is preferably processed by a software program in the control mechanism 124 (preferably a programmed computer). It is, of course, understood that analog to digital conversion is not a necessary limitation. The control mechanism 124 can be configured to receive an analog signal directly.

The control mechanism 124 determines whether stripping endpoint has occurred and sends a cessation signal 160 to the microwave plasma generator 106 if endpoint is detected, or if the endpoint is not detected within a predetermined time frame. The control mechanism 124 also provides transfer instructions 162 to a wafer transfer device 148 based on electronic signal 156. The transfer instructions 162 are generated for either the detection of stripping endpoint or for the rejection of the semiconductor substrate 104. The transfer instructions 162 will trigger the placement and retrieval of the semiconductor substrate 104 into the stripping chamber 102 and from the stripping chamber 102 after the test to another location for further processing. The electronic signals 122 for stage control are also sent by the control mechanism 124 for controlling motion of the movable stage 118.

Figure 3:
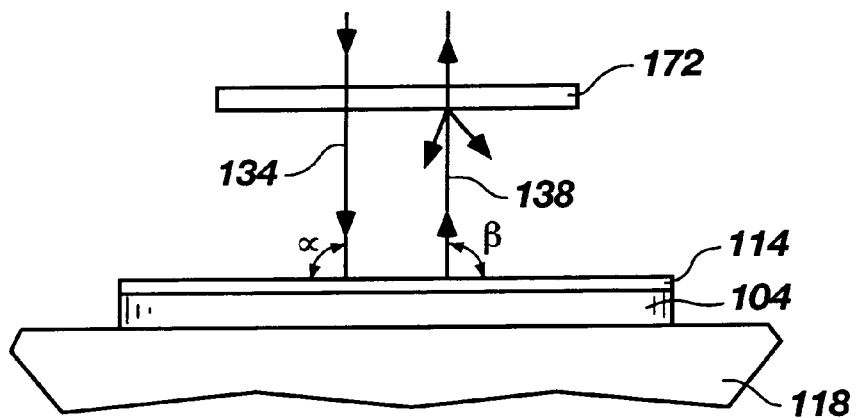
FIG. 3 is a side view of an alternate light detection configuration of the present invention.

As illustrated in FIG. 1, the beam 134 is shown striking the photo-resist material 114 on the semiconductor substrate 104 at the angle of incidence α of about 45 degrees and the emanated beam 138 is shown reflected at the angle of departure β of about 45 degrees. The incident angle α for the beam 134 and the departure angle β for the emanated beam 138 are preferably between 0 and 45 degrees. However, by using a dichromatic mirror 172 (a mirror which reflects wavelengths of less than a given value, and passes wavelengths greater than the given value) as shown in FIG. 3, the beam 134 and the emanated beam 138 may both pass through the same port, and incident angle α and the departure angle β are both 90 degrees (i.e., perpendicular to the semiconductor substrate 104). The emanated beam 138 is shown offset from the beam 134 for the sake of clarity.

The high energy lamp 136 is preferably a mercury or xenon lamp which produces high intensity, fluorescence-inducing illumination. The light output from the high energy lamp 136 may be filtered by a band pass or excitation filter 144 for removing wavelengths from the primary high energy beam 134 which do not stimulate fluorescence, reflect, or absorb in the semiconductor substrate 104.

As indicated, the method depends upon a difference in fluorescence or light absorption/reflectance between the material to be detected, e.g., the photo-resist and the underlying substrate. A wavelength of incident illumination is typically chosen which maximizes the difference in fluorescence, absorption, or reflectance. It is preferred to use fluorescence as the measured output, but light absorbance may be used when the material to be detected strongly absorbs a particular wavelength of radiation while the substrate strongly reflects the same.

It should be understood that references herein to light of a particular "wavelength" encompass wavelength bands that are "about" a particular wavelength. In other words, the term "a particular wavelength" may include wavelengths both slightly longer and shorter than the "particular wavelength".

Having thus described in detail preferred embodiments of the present invention, it is to be understood that the invention defined by the appended claims is not to be limited by particular details set forth in the above description, as many apparent variations thereof are possible without departing from the spirit or scope thereof.

What is claimed is:

1. A method for stripping endpoint detection of a photo-resist material on a substrate surface, comprising:

positioning a substrate within an etching chamber to receive illumination from a beam of generated light from a light source;

etching said photo-resist material on said substrate surface;

irradiating said photo-resist material and any exposed portions of said substrate surface with said beam of generated light;

collecting emanated light from the irradiated photo-resist material and said substrate surface portions;

filtering said emanated light to at least one wavelength indicative of said photo-resist material; and generating an electronic signal indicative of an intensity of said filtered light.

2. The method of claim 1, further comprising transmitting said electronic signal to a control mechanism for processing.

3. The method of claim 2, wherein said control mechanism generates an instruction to discontinue etching said photo-resist material on said substrate surface.

4. The method of claim 2, wherein said control mechanism generates an instruction for transmission to an automated substrate handling apparatus to control disposition of said substrate based on said indicated light intensity.

5. The method of claim 4, further comprising moving said substrate by said automated substrate handling apparatus to a location designated to receive substrates having the indicated light intensity.

6. The method of claim 5, further comprising the steps of sequentially positioning additional substrates to be irradiated by said beam of generated light for measurement of light reflected and flouresced from said substrates.

7. The method of claim 2, further comprising transmitting said electronic signal to a programmable computer for processing.

8. The method of claim 1, further comprising determining the presence of said material by detecting the presence of a selected wavelength of fluoresced light characteristic of said photo-resist material.

9. The method of claim 8, further comprising filtering said beam of generated light with a filter prior to irradiating said material to remove non-fluorescence producing light wavelengths from said beam of generated light.

10. The method of claim 1, further comprising determining the presence of said photo-resist material by detecting the absence of a given wavelength of light characteristically absorbed by said photo-resist material and characteristically reflected by said substrate.

11. The method of claim 10, further comprising filtering said beam of generated light through a filter prior to irradiating said substrate surface to limit light transmission to wavelengths substantially absorbed by said photo-resist material and substantially reflected by said substrate.

12. The method of claim 1, further comprising determining the presence of said photo-resist material by detecting the presence of a given wavelength of light characteristically reflected by said photo-resist material and characteristically absorbed by said substrate.

13. The method of claim 12, further comprising filtering said beam of generated light through a filter prior to irradiating said substrate surface to limit light transmission to wavelengths substantially reflected by said photo-resist material and substantially absorbed by said substrate.

14. The method of claim 1, further comprising determining the presence of said photo-resist material by detecting the presence of at least one wavelength band indicative of the presence of said photo-resist material.

15. The method of claim 1, wherein generating said electronic signal includes passage of said filtered emanated light through a photo-multiplier tube to generate said signal indicative of said light intensity.

16. The method of claim 1, wherein said substrate comprises a semiconductor substrate.

17. The method of claim 2, further comprising moving said substrate under said beam.

18. The method of claim 17, further comprising positioning said substrate on a movable stage for moving said substrate for detection testing of an entire surface of said substrate.

19. The method of claim 18, wherein movement of said movable stage is controlled by said control mechanism.

20. The method of claim 1, further comprising positioning said substrate on a rotating platform for rotating said substrate for detection testing of an entire surface of said substrate.

21. The method of claim 1, wherein said beam is a sheet beam.

22. The method of claim 21, wherein said sheet beam has a width at least as wide as a width of said substrate.

23. An apparatus for determining an endpoint for stripping of a material from a surface of a substrate, comprising:

a stripping chamber for receiving said substrate;

a microwave generator for generating at least one reactive species for delivery to said stripping chamber for etching said material;

a primary high energy light source;

first optical apparatus for forming a beam of high energy light and directing the high energy light to said material on said substrate;

second optical apparatus for collecting emanated light from said material as a secondary light beam and directing said secondary light beam through a band pass filter; and a light intensity sensing apparatus for receiving said filtered secondary light beam, measuring an intensity thereof, and generating an electric signal representative of said measured light intensity.

24. The apparatus of claim 23, further comprising a control mechanism for processing said electronic signal.

25. The apparatus of claim 24, further comprising an automated substrate handling apparatus for moving said substrate to and from said stripping chamber.

26. The apparatus of claim 25, further comprising a plurality of sites for selective movement of said substrate thereto from said stripping chamber by said automated substrate handling apparatus dependent upon the light intensity measurement from said substrate.

27. The apparatus of claim 23, further including a platform which is rotatable for measuring an entire surface of said substrate.

28. The apparatus of claim 23, further including a stage which is moveable for positioning said substrate for measuring an entire surface of said substrate.

29. The apparatus of claim 24, wherein said control mechanism comprises a computer programmed to receive and record said light measurement, instruct said movable stage to move said substrate, and instruct a robot to move said substrate to and from said movable stage.

30. The apparatus of claim 23, wherein said first optical apparatus comprises a lens and a primary band pass filter for restricting said beam of high energy light to a predetermined wavelength band.

31. The apparatus of claim 30, wherein said primary band pass filter comprises a filter for passing radiation which induces fluorescence in said material.

32. The apparatus of claim 30, wherein said primary band pass filter is configured to pass light wavelengths which are substantially absorbed by said material and substantially reflected by said substrate.

33. The apparatus of claim 30, wherein said primary band pass filter is configured to pass light wavelengths which are substantially reflected by said material and substantially absorbed by said substrate.

34. The apparatus of claim 30, further comprising a dichromatic mirror for reflecting said beam of high energy light through a lens to said surface of said substrate and for passing fluoresced and reflected light in a reverse direction.

35. The apparatus of claim 23, wherein said high energy light source comprises a mercury lamp.

36. The apparatus of claim 23, wherein said high energy light source comprises a xenon lamp.

37. The apparatus of claim 23, wherein said light intensity sensing apparatus comprises a silicon diode sensor which produces a light intensity measurement.

38. The apparatus of claim 37, further comprising a power meter for converting the light intensity measurement into a digital form.

39. The apparatus of claim 23, wherein said light intensity sensing apparatus comprises a photo-multiplier tube with output signal means.

40. The apparatus of claim 23, wherein said primary high energy beam is a sheet beam.

41. The apparatus of claim 40, wherein said sheet beam has a width at least as wide as a width of said substrate.

42. The apparatus of claim 23, wherein said material is a photo-resist material.

\* \* \* \* \*

UNITED STATES PATENT AND TRADEMARK OFFICE
CERTIFICATE OF CORRECTION

PATENT NO. : 5,969,805
DATED : October 19, 1999
INVENTOR(S) : David R. Johnson, Joe Lee Phillips, Todd C. Nielsen and Robert J. Hatfield It is certified that error appears in the above-identified patent and that said Letters Patent is hereby corrected as shown below:

Column 1,
Line 63, delete "is generated" at beginning of line and after "species" insert -- is generated --

Column 2,
Line 43, change "radials" to -- radicals --

Column 4,
Line 50, change "flourescing," to -- fluorescing, --

Column 7,
Line 9, change "steps" to -- step --
Line 12, change "flouresced" to -- fluoresced --
Line 17, after "said" insert -- photo-resist --
Line 22, at beginning of line before "material" insert -- photo-resist --

Column 10,
Line 1, delete "primary"
Line 2, after "energy" insert -- light --

Signed and Sealed this

Twelfth Day of November, 2002

Attest:

JAMES E. ROGAN
Attesting Officer
Director of the United States Patent and Trademark Office